United States Patent
Sucov et al.

(10) Patent No.: US 6,278,040 B1
(45) Date of Patent: Aug. 21, 2001

(54) RECEPTOR-DEFICIENT MICE AND CELL LINES DERIVED THEREFROM, AND USES THEREOF

(75) Inventors: Henry M. Sucov, San Diego; Ronald M. Evans; Kenneth R. Chien, both of La Jolla, all of CA (US)

(73) Assignees: The Salk Institute for Biological Studies, San Diego; The Regents of the University of Calif., Oakland, both of CA (US)

( * ) Notice: Subject to any disclaimer, the term of this patent is extended or adjusted under 35 U.S.C. 154(b) by 0 days.

(21) Appl. No.: 08/802,468

(22) Filed: Feb. 19, 1997

Related U.S. Application Data (63) Continuation of application No. 08/241,044, filed on May 10, 1994, now abandoned.

(51) Int. Cl.$^7$ ............................. C12N 15/09; C12N 15/63; C12N 15/00; C12N 5/00
(52) U.S. Cl. .................................. 800/18; 800/3; 800/21; 800/22; 800/25; 435/455; 435/463; 435/462; 435/320.1; 435/325
(58) Field of Search ................................... 800/18, 3, 21, 800/22, 25; 435/455, 463, 462, 320.1, 325

(56) References Cited

PUBLICATIONS

Evans, R.M., "The Steroid and Thyroid Hormone Receptor Superfamily" *Science* 240:889–895 (1988).
Green and Chambon, "Nuclear receptors enhance our understanding of transcription regulation" *Trends in Genetics* 4:309–314 (1992).
Kliewer et al., "Convergence of 9–cis retinoic acid and peroxisome proliferator signalling pathways through heterodimer formation of their receptors" *Nature* 358:771–774 (1992).
Mangelsdorf et al., "Characterization of three RXR genes that mediate the action of 9–cis retinoic acid" *Genes & Development* 6:329–344 (1992).
Miller–Hance et al., "In Vitro Chamber Specification during Embryonic Stem Cell Cardiogenesis" *J. Biol. Chem.* 268:25244–25252 (1993).
O'Brien et al., "Positional specification of ventricular myosin light chain 2 expression in the primitive murine heart tube" *Proc. Natl. Acad. Sci. USA* 90:5157–5161 (1993).
Schwab et al., "Human N–myc gene contributes to neoplastic transformation of mammalian cells in culture" *Nature* 316:160–162 (1988).
Sucov et al., "RXRα mutant mice establish a genetic basis for vitamin a signaling in heart morphogenesis" *Genes & Development* 8:1007–1018 (1994).
Thomas and Capecchi, "Site–Directed Mutagenesis by Gene Targeting in Mouse Embryo–Derived Stem Cells" *Cell* 51:503–512 (1987).
Yancopoulos et al., "N–myc can cooperate with ras to transform normal cells in culture" *Proc. Natl. Acad. Sci. USA* 82:5455–5459 (1985).
Kubalak, et al., "Chamber Specification of Atrial Myosin Light Chain–2 Expression Precedes Septation during Murine Cardiogenesis" *J. Biochem* 269:16961–16970 (1994).
Moreadith et al., J. Mol. Med., vol. 75, pp. 208–216, 1997.*
Lufkin et la., PNAS 90 :7225–7229 (1993).*
Li et al., PNAS 90: 1590–1594 (1993).*
Lohnes et al., Cell 73: 643–658 (1993).*

* cited by examiner

*Primary Examiner*—Jill Martin
(74) *Attorney, Agent, or Firm*—Gray Cary Ware & Freidenrich LLP; Stephen E. Reiter (57) ABSTRACT

In accordance with the present invention, there are provided targeted loss of function mutant mice which express less than endogenous levels of at least one member of the steroid/thyroid superfamily of receptors in at least one specific tissue type. For example, mutations in the RXRα gene in mouse germlines are lethal in the embryonic stage between E13.5 and E16.5 when bred to homozygosity. The major defect responsible for this lethal effect is hypoplastic development of the ventricular chambers of the heart, which is manifest as a grossly thinned ventricular wall with concurrent defects in ventricular septation. This phenotype is identical to a subset of the effects of embryonic vitamin A deficiency, and therefore establishes RXRα as a genetic component of the vitamin A signaling pathway in cardiac morphogenesis. The cardiac outflow tracts and associated vessels, which are populated by derivatives of the neural crest and which are also sensitive to vitamin A deficiency, are normal in homozygous embryos, indicating the genetic independence of ventricular chamber development. Hepatic differentiation was dramatically but transiently retarded, yet is histologically and morphologically normal. These results ascribe an essential function for the RXRα gene in embryonic development, and provide the first evidence of a requirement for RXR in one of its predicted hormone response pathways.

4 Claims, 2 Drawing Sheets

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
       (A) LENGTH: 71 amino acids
       (B) TYPE: amino acid
       (D) TOPOLOGY: linear (ii) MOLECULE TYPE: protein (v) FRAGMENT TYPE: internal (xi) SEQUENCE DESCRIPTION: SEQ ID NO: 1:

Cys Xaa Xaa Cys Xaa Xaa Asp Xaa Ala Xaa Gly Xaa Tyr Xaa Xaa Xaa
1               5                   10                  15

Xaa Cys Xaa Xaa Cys Lys Xaa Phe Phe Xaa Arg Xaa Xaa Xaa Xaa Xaa
            20                  25                  30

Xaa Xaa Xaa Xaa Xaa Cys Xaa Xaa Xaa Xaa Xaa Xaa Xaa Xaa Xaa Cys
        35                  40                  45

Xaa Xaa Xaa Lys Xaa Xaa Arg Xaa Xaa Cys Xaa Xaa Cys Arg Xaa Xaa
    50                  55                  60

Lys Cys Xaa Xaa Xaa Gly Met
65                  70

(2) INFORMATION FOR SEQ ID NO: 2:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 2:

GCGTGCAATC CATCTTGTTC AATG                                           24

(2) INFORMATION FOR SEQ ID NO: 3:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 3:

TGCCCATCCC TCAGGAAATA TGG                                            23

(2) INFORMATION FOR SEQ ID NO: 4:

(i) SEQUENCE CHARACTERISTICS:
       (A) LENGTH: 34 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 4:

```
CTCAAGCTTC CTGCCCATCC CTCAGGAAAT ATGG                            34
```

(2) INFORMATION FOR SEQ ID NO: 5:

(i) SEQUENCE CHARACTERISTICS:
        (A) LENGTH: 26 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO: 5:

```
TAGAGGATGG GTGAACTTAA TGACAA                                     26
```

(2) INFORMATION FOR SEQ ID NO: 6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO: 6:

```
ATCTCCATGA GGAAGGTGTC                                            20
```

(2) INFORMATION FOR SEQ ID NO: 7:

(i) SEQUENCE CHARACTERISTICS:
        (A) LENGTH: 22 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO: 7:

```
CTTGAAGAAG AACAGGTGCT CC                                         22
```

(2) INFORMATION FOR SEQ ID NO: 8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO: 8:

```
TGGGCAGCTG CACTCTCCTA T                                          21
```

(2) INFORMATION FOR SEQ ID NO: 9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO: 9:

```
AATGAGAACG AGGTGGAGTC CA                                         22
```

(2) INFORMATION FOR SEQ ID NO: 10:

```
    (i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 10:

GCACTTCTCC TCCCTACCTC TG                                              22
```

RECEPTOR-DEFICIENT MICE AND CELL LINES DERIVED THEREFROM, AND USES THEREOF

This application is a continuation of U.S. patent application Ser. No. 08/241,044, filed May 10, 1994, now abandoned.

ACKNOWLEDGEMENT

This invention was made with Government support under Grant No. HD-27183 and HD-46345, awarded by the National Institutes of Health. The Government has certain rights in the invention.

FIELD OF THE INVENTION

The present invention relates to transgenic mice and uses therefor. In a particular aspect, the present invention relates to transgenic mice which are deficient in one or more members of the steroid/thyroid superfamily of receptors, as well as various uses therefor.

BACKGROUND OF THE INVENTION

The steroid/thyroid superfamily of receptors comprises a broad range of regulatory compounds which are involved in a wide range of regulatory processes. For example, retinoic acid (RA) and related vitamin A derivatives (retinoids) comprise a collection of molecules that serve as signals to trigger and modulate complex morphogenic events during vertebrate development. In addition, retinoids serve to maintain homeostasis in the adult. Retinoids display profound effects on cell differentiation and proliferation, and have been used extensively to influence differentiation in organ and cell culture systems (reviewed by Tabin in Cell 66:199–217 (1991); and Brockes in Neuron 2:1285–1294 (1989)). Retinoids can block the effects of tumor promoters in cell culture and have been used in chemoprevention, as well as in the primary treatment, of certain solid tumors and leukemias in humans (see, for example, Hong and Itri, "Retinoids and Human Cancer" in The Retinoids: Biology, Chemistry and Medicine, 2nd Edition, M. B. Sporn, A. B. Roberts and D. S. Goodman (eds.), Raven Press Ltd.: New York. (1994); and Warrell et al. in New Engl. J. Med. 324:1385–1393 (1991)).

Exposure of vertebrate embryos to retinoic acid leads to a variety of teratogenic effects, depending on the time and dose of the exposure (see, for example, Linney and LaMantia, "Retinoid signaling in mouse embryos" in Advances in Developmental Biology, Vol. 3, in press (1994); and Morris-Kay (ed.) in Retinoids in Normal Development and Teratogenesis, Oxford University Press: Oxford (1992)). The most prominent target tissues include the heart, the axial skeleton, cranial and cardiac neural crest derived tissues, and the limbs. Paradoxically, vitamin A deficiency leads to an overlapping spectrum of defects, indicating a requirement for retinoids during normal development as well as a common target whose proper action is essential for the execution of developmental programs. A central question arising from these observations is how a simple molecule such as retinoic acid can lead to such diverse biological effects.

A great deal of this complexity can be explained by the observation that retinoid receptors are members of the nuclear receptor superfamily of ligand-dependent transcription factors (see, for example, Evans in Science 240:889–895 (1988); and Green and Chambon in Trends in Genet. 4:309–314 (1988)). Retinoid receptors comprise two distinct subfamilies composed of three retinoic acid receptors (RARs) and three evolutionarily distinct retinoid X receptors (RXRs) (see Mangelsdorf et al. in Genes and Devel. 6:329–344 (1992) and references therein). The RARs and RXRs share overlapping ligand specificity, i.e., both receptors bind 9-cis retinoic acid with high affinity, whereas only the RARs bind all-trans retinoic acid (see Heyman et al. in Cell 68:397–406 (1992); and Levin et al. in Nature 355:359–361 (1992)). It has been shown in vitro that RXRs are able to bind DNA as homodimers, whereas the RARs (as well as receptors for other hormones or hormone-like compounds, e.g., thyroid hormones (TRs), vitamin D (VDR), and peroxisome proliferators (PPARs)) form heterodimers with RXRs. Such heterodimers bind DNA in a highly cooperative fashion (see, for example, Yu et al. in Genes and Dev. 6:1783–1798 (1991); Kliewer et al. in Nature 355:446–449 (1992); Leid et al. in Cell 68:377–395 (1992); Marks et al. in EMBO J. 11:1419–1435 (1992); Zhang et al. in Nature 355:441–446 (1992); and Kleiwer et al. in Nature 358: 771–774 (1992)). The RXRs, therefore, apparently play a central role in mediating multiple hormonal signaling pathways.

Each RXR (and RAR) subtype is differentially expressed in a spectrum of tissues during normal embryonic development and beyond (see Mangelsdorf et al., supra). The RXRα gene, for example, is abundant in the intestine, heart, muscle, liver, kidney, and skin of the adult, whereas the RXRβ gene is expressed at a low level in nearly all tissues. RXRγ shows the most restricted pattern of expression in both the embryo and adult, with highest levels in mesoderm and its derivatives and in parts of the nervous system.

To allow a more complete understanding of the diverse role of members of the steroid/thyroid superfamily of receptors (e.g., retinoid receptors) in development and/or physiology, it would be desirable to be able to correlate defects associated with ligand (e.g., retinoid) excess or deficiency with the presence or absence of individual receptor gene products.

BRIEF DESCRIPTION OF THE INVENTION

In accordance with the present invention, transgenic mice have been developed through the introduction of specific mutations into the germline thereof. Such mice enable the functional analysis of individual receptor genes to be carried out in vivo. For example, individual mutations of the RARα and RARγ genes have surprisingly been found not to be lethal in the embryonic stage. In fact, the resulting mutants display fairly subtle phenotypes.

In contrast, mutation of the RXR gene has been found to result in embryonic lethality, apparently due to hypoplastic development of the ventricular chambers of the embryonic heart. This mutation also results in strikingly delayed development of the embryonic liver. This delayed development is unlikely, however, to be causal to the embryonic lethality. These results provide the first genetic evidence for a role of RXRs in retinoid signaling and establish an essential role for this receptor in embryogenesis.

BRIEF DESCRIPTION OF THE FIGS.

FIG. 2 illustrates the strategy used for the targeted disruption of the RXR(X gene. FIG. 2A illustrates the wildtype RXRα gene. For simplicity, only the A2, B/Cl, and C2 exons, represented by filled boxes, are shown.

FIG. 2C illustrates the mutated RXRα locus following homologous recombination. Fragments A and B used for probes on genome blots are indicated in small boxes, above the predicted genomic fragments following BamHI, HindIII or EcoRI digestion. PCR primers used to verify homologous recombination are indicated as horizontal arrows. Restriction sites are: B, BamHI; E, EcoRI; H3, HindIII; N, NotI; R5, EcoRV; S, SalI; and Xb, XbaI.

DETAILED DESCRIPTION OF THE INVENTION

In accordance with the present invention, there are provided transgenic mice which express less than endogenous levels of at least one member of the steroid/thyroid superfamily of receptors in at least one specific tissue type.

As employed herein, the phrase "endogenous levels" refers to levels of expression and tissue distributions observed for a given member of the steroid/thyroid superfamily of receptors in wildtype host organisms. Thus, "less than" endogenous levels refers to reduction of receptor expression in any given tissue where the receptor is normally expressed such that the overall level of receptor expression in the transgenic mouse of the invention (or cells derived therefrom) is reduced relative to the level of expression in wildtype hosts.

As employed herein, the phrase "member(s) of the steroid/thyroid superfamily of receptors" refers to all of the various isoforms of hormone binding proteins that operate as ligand-dependent transcription factors, including members of the steroid/thyroid superfamily of receptors for which specific ligands have not yet been identified (referred to hereinafter as "orphan receptors"). Each such receptor protein has the intrinsic ability to bind to a specific DNA sequence (i.e., regulatory sequence) associated with a target gene. The transcriptional activity of the gene is modulated by the presence or absence of the cognate hormone (ligand) as a result of binding of ligand to receptor, enabling interaction of receptor with the regulatory sequence.

The DNA-binding domains of all members of this superfamily of receptors are related, consisting of 66–68 amino acid residues, and possessing about 20 invariant amino acid residues, including nine cysteines. A member of the superfamily can be characterized as a protein which contains these diagnostic amino acid residues, which are part of the DNA-binding domain of such known steroid receptors as the human glucocorticoid receptor (amino acids 421–486), the estrogen receptor (amino acids 185–250), the mineralocorticoid receptor (amino acids 603–668), the human retinoic acid receptor (amino acids 88–153), and the like. The highly conserved amino acids of the DNA-binding domain of members of the superfamily are as follows:

Cys-X-X-Cys-X-X-Asp*-X-Ala*-X-Gly*-X-Tyr*-X-X-X-X-Cys-X-X-Cys-Lys*-X-Phe-Phe-X-Arg*-X-X-X-X-X-X-X-X-(X-X-) Cys-X-X-X-X-X-(X-X-X-) Cys-X-X-X-Lys-X-Arg-X-X-Cys-X-X-Cys-Arg*-X-X-Lys*-Cys-X-X-X-Gly*-Met (SEQ ID No 1);

wherein X designates non-conserved amino acids within the DNA-binding domain; the amino acid residues denoted with an asterisk are residues that are almost universally conserved, but for which variations have been found in some identified hormone receptors; and the residues enclosed in parenthesis are optional residues (thus, the DNA-binding domain is a minimum of 66 amino acids in length, but can contain several additional residues).

Exemplary members of the steroid/thyroid superfamily of receptors (including the various isoforms thereof) include steroid receptors such as glucocorticoid receptor, mineralocorticoid receptor, progesterone receptor, androgen receptor, vitamin $D_3$ receptor, and the like; plus retinoid receptors, such as the various isoforms of RAR (e.g., RARα, RARβ, or RARγ), the various isoforms of RXR (e.g., RXRα, RXRβ, or RXRγ), and the like; thyroid receptors, such as TRα, TRβ, and the like; insect derived receptors such as the ecdysone receptor, and the like; as well as other gene products which, by their structure and properties, are considered to be members of the superfamily, as defined hereinabove, including the various isoforms thereof (even though ligands therefor have not yet been identified; such receptors are referred to as "orphan receptors"). Examples of orphan receptors include HNF4 (see, for example, Sladek et al. in *Genes & Development* 4:2353–2365 (1990)), the COUP family of receptors (see, for example, Miyajima et al. in *Nucleic Acids Research* 16:11057–11074 (1988); and Wang et al. in Nature 340:163–166 (1989)), COUP-like receptors and COUP homologs, such as those described by Mlodzik et al. in *Cell* 60:211–224 (1990) and Ladias et al. in *Science* 251:561–565 (1991), various isoforms of peroxisome proliferator-activated receptors (PPARs; see, for example, Issemann and Green in Nature 347:645–650 (1990)), the insect derived knirps and knirps-related receptors, and the like.

Transgenic mice contemplated by the present invention include mice wherein less than endogenous levels of one or more members of the steroid/thyroid superfamily of receptors is expressed throughout the mouse (i.e., expression of receptor is reduced in all tissues where normally expressed). Additional transgenic mice contemplated by the present invention include mice wherein expression of a specific member(s) of the steroid/thyroid superfamily of receptors occurs at less than endogenous levels in selected tissues of the mice.

Exemplary transgenic mice contemplated by the present invention include mice wherein at least one member of the steroid/thyroid superfamily of receptors selected from RARα, RARβ or RARγ is expressed at less than endogenous levels; or wherein at least one member of the steroid/thyroid superfamily of receptors selected from RXRα, RXRβ or RXRγ is expressed at less than endogenous levels; or wherein at least one member of the steroid/thyroid superfamily of receptors selected from GR, MR, ER, PR or TR is expressed at less than endogenous levels; or wherein at least one member of the steroid/thyroid superfamily of receptors selected from ERR1, ERR2, HNF4, PPARα, PPARβ, PPARγ, COUP or COUP-like receptors, as well as any other orphan receptor, is expressed at less than endoqenous levels.

Presently preferred transgenic mice according to invention are those wherein the steroid/thyroid superfamily of receptors is selected from the retinoic acid receptor family of receptors (e.g., RARα) or the retinoid X receptors (e.g., RXRα).

In RXRα-deficient homozygous mutants of the invention, cardiogenesis appears to result in failure of normal ventricular muscle to develop sufficiently to meet the demands of the growing embryo. Formation of the mature ventricular chamber requires the development of extensive ventricular trabeculation and of the dense compact muscle layer in the ventricular free wall. The increased thickness of the ventricular wall allows the myocardium to generate sufficient mechanical force to maintain blood flow through the growing embryo. As described herein, lack of RXRα permits formation of a trabeculated, yet dysmorphic ventricular chamber, with the thickness of the ventricular wall resembling the relatively thin-walled atrial chamber. It is possible that the development of the compact muscular layer of the ventricles is dependent on the RXRα signaling pathway, while the formation of the inner trabecular layer may rely on a compensating or alternative pathway. Although the RXRα phenotype may simply be due to a defect in the proliferative capacity of fully differentiated ventricular muscle cells, the primary defect may instead reflect an arrest or delay in the sequential maturation of ventricular muscle cell lineages (Kubalak et al., "Chamber specification of MLC-2a expression precedes septation during murine cardiogenesis" in *J. Biol. Chem.* press (1994)).

The poor development of the muscular ventricular septum seen in homozygous embryos is most likely accounted for by the lack of ventricular wall enlargement. The septum is formed by two processes. The trabeculae condense at the interventricular groove which denotes the future boundary of the developing right and left ventricular chambers. In addition, the medial walls of the expanding ventricles fuse together and grow inward, forming the major muscular portion of the septum. Most likely, it is this latter process which is disturbed in the RXRα embryos. Although the septum is the thickest portion of the ventricle in the normal E14.5 embryo, in RXRα homozygotes it appears to be simply a fenestrated sheet of trabeculae with little contribution of the muscular tissue normally derived from proliferation of the compact zone of the ventricle wall. A consequential lack of fusion of the endocardial cushions to the basal portion of this incomplete septum results in the observed ventricular septal defects.

Congenital cardiovascular malformations represent the single largest group of congenital defects in newborn human infants, affecting 1/200 live births on an annual basis. Of these, ventricular septal defects comprise almost a third of these cases, and represent the most frequent cardiac malformation in humans (Friedman, "Congenital heart disease in infancy and childhood; acquired heart disease in infancy and childhood" in Heart *Disease; a textbook of cardiovascular medicine,* Braunwald, E. (ed), third edition, pp 895–918, W. B. Saunders: Philadelphia (1988)). Recent advances have revealed an early patterning of the ventricular segment of the primitive murine heart tube at day E8.0 (O'Brien et al. in *Proc. Natl. Acad. Sci. USA* 90:5157–5161 (1993)) and ventricular chamber specification can occur independent of heart tube formation in embryonic stem cell models of cardiogenesis (Miller-Hance et al. in *J. Biol. Chem.* 268:25244–25252 (1993)).

Utilizing both positive and negative chamber-specific markers, sequential stages of maturation of ventricular muscle cell lineages have been elucidated (Kubalak et al., supra) and candidate regulatory factors and pathways have recently been identified (Chien et al. in *Ann. Rev. Physiol* 55:77–95 (1993); Zhu et al. in Mol. *Cell. Biol.* 13:4432–4444 (1993); Lints et al. in *Development* 119:419–431 (1993) ; Komura and Izumo in *Proc. Natl. Acad. Sci. USA* 90:8145–8149 (1993); Yu et al. in *Genes and Dev.* 6:1783–1798 (1992); and Pollock and Treisman in *Genes and Dev.* 5:2327–2341 (1991)). The question arises as to where retinoic acid and RXRα intersect with these other pathways, and whether the cardiac phenotype reflects maturational arrest in ventricular muscle cell lineages. RXRα deficient mice of the present invention provide a unique and valuable experimental model system to further dissect normal and abnormal ventricular chamber development at a molecular level.

Transgenic mice can readily be prepared employing techniques known to those of skill in the art. Thus, the coding region of any member of the steroid/thyroid superfamily of receptors can be disrupted employing techniques well known to those of skill in the art, e.g., by homologous recombination, transgene insertional mutagenesis, spontaneous mutagenesis, induced mutagenesis (e.g., chemically induced or induced by irradiation), and the like (see, for example, Thomas and Capecchi in Cell 51: 503–512 (1987), and Example 6)). Homologous recombination is presently preferred because this method allows one to specifically target a single gene of interest for mutation.

The disrupted coding sequence derived from a member of the steroid/thyroid superfamily can be introduced by suitable means (e.g., electroporation, microinjection, and the like) into suitable embryonic stem cells (e.g., the Jl line of embryonic stem cells, see Example 6), and colonies isolated after selection. The resulting colonies are introduced into suitable host animals and allowed to colonize the germline. Cell lines and chimeric animals can be genotyped by way of Southern blots, by PCR analysis, and the like.

In accordance with another embodiment of the present invention, there are provided cell lines derived from the above-described transgenic mice.

As employed herein, the phrase "cell lines" is readily understood by those of skill in the art to mean a permanently established cell culture which will proliferate indefinitely given appropriate fresh medium and space. The generation of cell lines derived from the above-described transgenic mice can be readily accomplished by those of skill in the art (see, for example, Schwab et al. in *Nature* 316:160–162 (1985); and Yarcopoulos et al. in *Proc. Natl. Acad. Sci. USA* 82:5455 5459 (1985)).

In accordance with yet another embodiment of the present invention, there is provided a method for determining the role of at least one member of the steroid/thyroid superfamily of receptors in development and/or physiology, said method comprising:

generating a transgenic mouse which expresses less than endogenous levels of at least one member of the steroid/thyroid superfamily of receptors in at least one specific tissue type, and observing phenotypic changes in said mouse, relative to a wild-type animal at comparable stage of development.

Phenotypic changes can be observed visually (e.g., where gross defects are caused by altered expression of a member of the steroid/thyroid superfamily of receptors), or by a variety of assays as are readily available to those of skill in the art.

As employed herein, the phrase "role . . . in development and/or physiology" refers to any change in normal development and/or normal physiological responses which is directly attributable to altered levels of expression of member(s) of the steroid/thyroid superfamily of receptors.

In accordance with a further embodiment of the present invention, there is provided a method to determine the selectivity of a ligand for a specific member of the steroid/thyroid superfamily of receptors, said method comprising:

treating a transgenic mouse deficient in said specific receptor species with said ligand, and monitoring said transgenic mouse for response to exposure to said ligand.

"Monitoring" contemplated by this aspect of the present invention involves comparing the response of mutant mice to ligand, relative to the response of normal mice to the same ligand. Thus, the specific analysis to be carried out depends on the ligand employed and the receptor with which it interacts. Those of skill in the art recognize that such monitoring can be carried out in a variety of ways, e.g., by visual observation of the transgenic animal for evidence of reaction to said ligand, and the like.

In accordance with a still further embodiment of the present invention, there is provided a method for the treatment of cardiac malfunction, e.g., hypertrophy, ischemia, and the like. The invention method comprises administering an effective amount of a retinoid compound to a mammalian subject exhibiting symptoms of cardiac malfunction, e.g., cardiac hypertrophy, ischemia, and the like.

Retinoid compound compounds contemplated for use in accordance with this aspect of the invention include such naturally occurring retinoids as all trans retinoic acid, 9-cis-retinoic acid, and the like, as well as synthetic retinoids (see, for example, *Chemistry and Biology of Synthetic Retinoids,* Dawson and Okamura, eds., CRC Press, Inc. (1990)).

For administration, the above-described retinoid compounds can be incorporated into a pharmaceutically acceptable formulation. Those of skill in the art can readily determine suitable dosage levels when the above-described retinoid compounds are so used.

A paradox to come out of the original discovery of the RXRs is their dual ability to serve as homodimeric receptors in response to 9-cis retinoic acid as well as to serve as heterodimeric partners for hormonal signaling mediated by other members of the steroid/thyroid superfamily of receptors, e.g., retinoic acid receptors (RARs), thyroid hormone receptors (TRs) and vitamin $D_3$ receptors (VDRs). Thus, in principle, the RXRs can mediate retinoid signaling via two different pathways, as well as participate in nonretinoid signaling via other receptor partnerships. While previous studies have been suggestive of the potential importance of RXR in hormonal signaling, there is no direct evidence for its essential role in any of these responses. Accordingly, the data presented herein provides unequivocal evidence as to the necessary role of RXRα in normal embryogenesis.

An important question arising out of these observations is whether this RXR deficiency is a consequence of a failure to transmit a hormonal signal and if so, which pathway is affected. Suggestive evidence comes from classical studies of nutritional deficiency, which indicate that vitamin A deficiency results in the same type of embryonic cardiac defects observed in RXRα mutant embryos. In one study (Wilson and Warkany in *Am. J. Anat.* 85:113–155 (1949)), approximately half of all affected embryos displayed hypoplastic ventricular chambers, with ventricular septal defects, identical to the phenotype described here. In contrast, fetal thyroid hormone deficiency produces minimal effects on growth or maturation, with replacement required only post-natally (see, for example, Letarte et al., "Chemical, biochemical and radiological features of neonatal hypothyroid infants" in *Neonatal Thyroid Screening,* G. N. Burrow and J. H. Dussault (eds.), pp. 225–236, Raven Press: New York (1980); and Fisher, "Hypothyroidism in infants and children" in *The Thyroid,* S. Ingbar and L. Braverman (eds.), Lippincott Co., Philadelphia, pp 1404–1411 (1986)). Similarly, inability to respond to vitamin $D_3$ due to a mutation in the VDR produces a normally developed embryo with rickets seen as a postnatal effect (Huqhes et al. in *Science* 242:1702–1705 (1988)). The concordance of the RXRα phenotype with vitamin A deficiency suggests that a retinoid-dependent pathway is likely to be compromised in the mutant background, and implicates either an RXR homodimer or RXR-RAR heterodimer process. These observations indicate an essential role for RXRα in vitamin A signalling and provide the first evidence of a requirement for RXR in one of its predicted hormone response pathways. Because delayed development of the liver is not a phenotype associated with vitamin A deficiency (nor $T_3$ or $D_3$ deficiency) this defect is likely due to a failed heterodimer formation with another RXR partner, possibly PPAR which is abundantly expressed in the liver (Issemann and Green, supra).

Previous studies (Mangelsdorf et al., supra) have documented the expression of RXRα mRNA in the adult heart, and while in situ hybridization studies have so far not detected expression in the embryonic heart, the expression of RXRα has been confirmed in E8.5 heart tubes and E12.5 and E13.5 ventricles by RT-PCR. Further, there is indirect functional evidence for the expression of RXR in the embryonic heart: a retinoic acid responsive transgene is both basally and inducibly expressed in ventricular myocytes at E12.5 and earlier, and a similar reporter gene is RA-inducible in microinjected cultured E14.5 ventricular myocytes. These observations strongly support the proposal that the ventricular defect is a probable consequence of the absence of RXRα in the differentiating heart itself, as opposed to a secondary effect. It also should be noted that while normal cardiac development proceeds from E7.5 to birth, the mutant hearts become dysmorphic by E12.5, indicating a putative temporal boundary for the requirement for RXRα expression.

The RXRα gene is abundantly expressed in other tissues of the embryo. Histological analysis indicates that these are normal in appearance in homozygous embryos (up to the time of death), with the only defect being the delayed growth of the liver. While histologically normal, it has not yet been determined whether any of these tissues display normal function. The RXRα gene may be required for certain gene regulatory processes which do not relate to morphogenesis but rather to the physiology of the organ. It should be possible to address this issue by monitoring the expression of specific markers for these tissues, some of which are known to be under retinoid control (see, for example, Kliewer et al. in *Nature* 358:771–774 (1992)).

The spectrum of tissues which utilize retinoid signaling, as delimited by vitamin A deficiency and retinoid teratology experiments, is far larger than can be accounted for by the known defects in the already established retinoid receptor gene mutations. The inference, in fact, from the gene knockout experiments described herein is that the defects observed tend to be far less widespread than the expression patterns might indicate. The most likely explanation is that there is considerable redundancy in expression and function between the receptor genes, so that mutation of a single gene does not compromise most tissues. The defects which are observed may represent either unique spatial expression of a given receptor gene, or a requirement for a unique functional property of a given receptor protein.

The invention will now be described in greater detail by reference to the following non-limiting examples.

EXAMPLE 1

Preparation of Targeting Constructs

Figure 1:
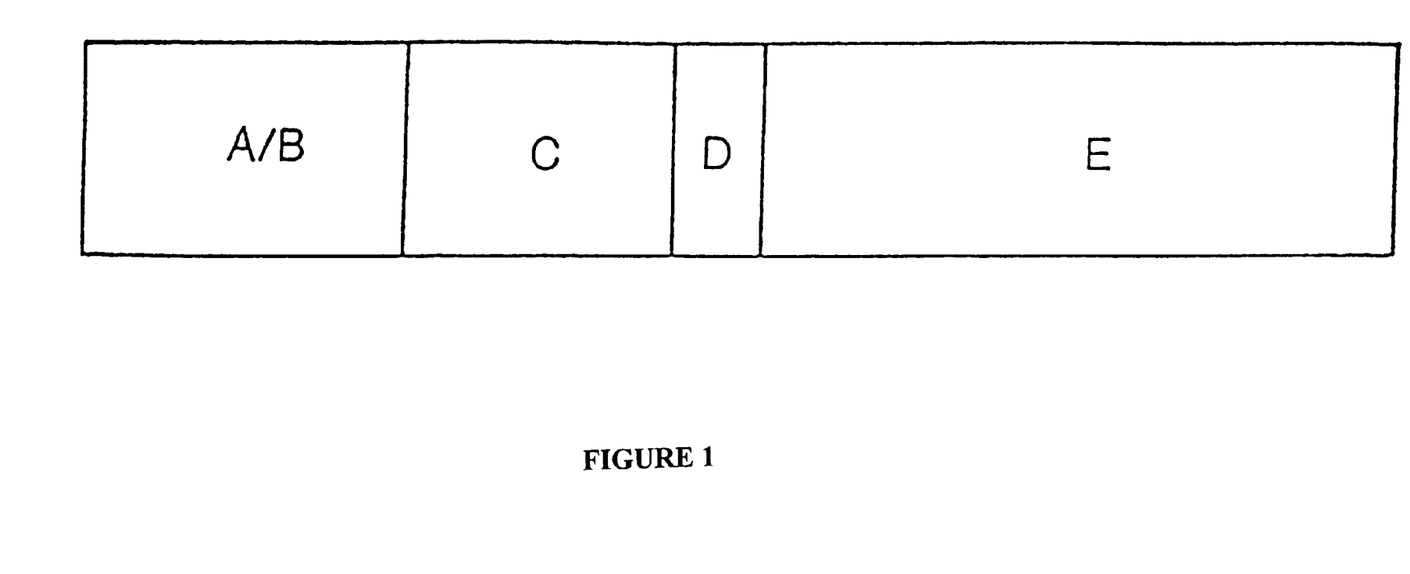
FIG. 1 is a schematic diagram of a generalized receptor of the steroid/thyroid superfamily.

RXRα genomic clones were isolated from a mouse 129/ Sv genomic library. The targeting construct represents 15 kb to the 5' side and 1.0 kb to the 3' side of the third exon, which encodes the B and the first part of the C (DNA binding) domains of the receptor (see FIG. 1). A PGK-neo cassette was introduced in the opposite orientation with respect to the RXRα gene between an EcoRV site in the exon and an XbaI site in the intron approximately 0.3 kb downstream.

EXAMPLE 2

Preparation of Founder Cells

ES cells of the J1 line (see Li et al. *Cell* 69:915–926 (1992)) were grown on a feeder layer of G418-resistant embryonic fibroblasts (derived from E13.5 embryos hoterozygous for a viable mutation in the RARa1 gene (Li et al. in *Proc. Natl. Acad. Sci.* USA 90:1590–1594 (1993)). ES cells were electroporated with NotI-linearized targeting construct under conditions as previously described (see Li et al., supra (1992)). Cells were selected with G418 and FIAU at concentrations of 175 µg/ml (active form) and 0.2 µM, respectively; individual colonies were picked after 8 days of selection and expanded for analysis. Correctly targeted cells were injected into C57Bl/6 blastocysts to create chiermic male founders, which were mated to C57Bl/6 females to achieve germline transmission of the targeted allele.

EXAMPLE 3

Genotyping

Two probes were used for screening ES colonies and for initial screening of animals. Probe A is contained in the targeting construct and represents the 1.0 kb 3' homology fragment (see FIGS. 2A and 2C). Probe B lies outside the targeting construct (see FIGS. 2A and 2C). Genomic DNA from ES cells or from mouse tails was restriction digested, electrophoresed, blotted, and probed by standard procedures. PCR primers derived from the neo gene and from sequence outside the targeting construct in the fourth intron were used to confirm results from Southern blots; a 1.7 kb amplification product was seen only from the targeted allele.

Routine genotyping of animals and of embryos was subsequently done by PCR using a combination of three primers; the neo primer referred to above (see SEQ ID NO:2), a primer from the B domain of the RXRα gene which is deleted in the targeted allele (see SEQ ID NOs:3 or 4), and a common primer from within the third intron (see SEQ ID NO:5); this results in the simultaneous amplification of both the wildtype and the targeted alleles as fragments of 600 and 900 bp, respectively, which can be easily resolved by electrophoresis. The sequence of the primers used is presented below:

The neo specific antisense primer:
  5'-GCGTGCAATC CATCTTGTTC AATG (SEQ ID NO:2)

Primer from the B domain of the RXRα gene which is deleted in the targeted allele:
  5'-TGCCCATCCC TCAGGAAATA TGG (SEQ ID NO:3), or
  5'-CTCAAGCTTC CTGCCCATCC CTCAGGAAAT ATGG (SEQ ID NO:4)

Common antisense primer from within the third intron (i.e., the intron between the B/C1 and C2 exons):
  5'-TAGAGGATGG GTGAACTTAA TGACAA (SEQ ID NO:5)

Embryos were individually isolated and genotyped by extraction and analysis of yolk sac DNA.

EXAMPLE 4

RT-PCR

Embryos were isolated at E13.5 and immediately homogenized individually in 4 ml of guanidinium thiocyanate buffer; total RNA was isolated as previously described by Chomczynski and Sacchi in *Anal. Biochem.* 162:156–159 (1987). Yolk sac DNA was extracted separately for genotyping. 1 µg of total RNA from wildtype, heterozygous, and homozygous embryos was reverse transcribed using an RXR-specific gene primer derived from the ligand binding domain (LBD) of the protein coding region (which is conserved between the RXRα and RXRβ genes, see SEQ ID NO:6). PCR amplification utilized a common antisense primer from the LBD (see SEQ ID NO:7), and sense primers from exons 2 and 5 (domains A2 and D) of the RXRα gene (see SEQ ID NOs:8 and 9, respectively), domain D of the RXRβ gene as a control (see SEQ ID NO:10), and a neo-specific coding region primer (see SEQ ID NO:2). Typical PCR reactions contained cDNA equivalent to 30 ng of total RNA, 200 ng each primer, and proceeded for 45 cycles. For analysis of RXRα expression in the heart, RNA was isolated as above from heart tubes of wild type E8.5 embryos and from ventricles of wild type E12.5 and E13.5 embryos, and reverse transcribed and amplified as above using the exon 5 sense primer. Parallel RNA samples were amplified without prior reverse transcription as controls. The sequence of the primers used is presented below:

RXR-specific reverse transcriptase gene primer:
  5'ATCTCCATGA GGAAGGTGTC (SEQ ID NO:6)

Common antisense primer from the LBD:
  5'-CTTGAAGAAG AACAGGTGCT CC (SEQ ID NO:7)

Sense primer from exon 2 (domain A2) of the RXRα gene:
  5'-TGGGCAGCTG CACTCTCCTA T (SEQ ID NO:8)

Sense primer from exon 5 (domain D) of the RXRα gene:
  5'-AATGAGAACG AGGTGGAGTC CA (SEQ ID NO:9)

Domain D of the RXRβ gene (as a control):
  5'-GCACTTCTCC TCCCTACCTC TG (SEQ ID NO:10).

EXAMPLE 5

Histology

Embryos were isolated and immediately fixed in 10% formalin in PBS, and stored at room temperature. Embryos were dehydrated, paraffin-embedded, sectioned at 5 or 10 micron thicknesses, and stained with hematoxylin-eosin.

EXAMPLE 6

Targeted Disruption of the RXRα Gene

Figure 2A:
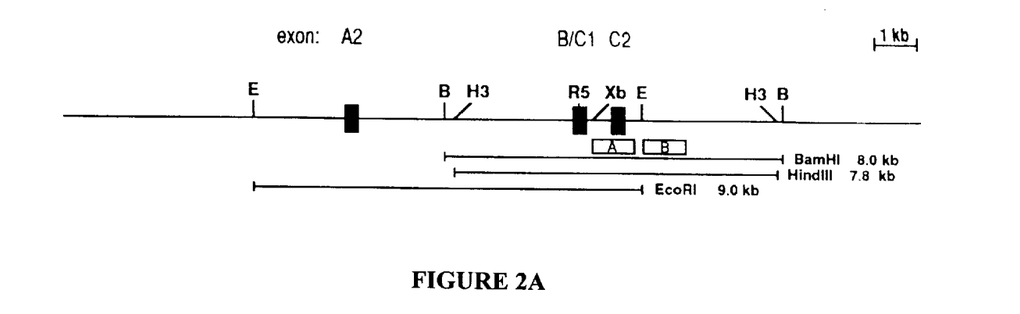
Figure 2B:
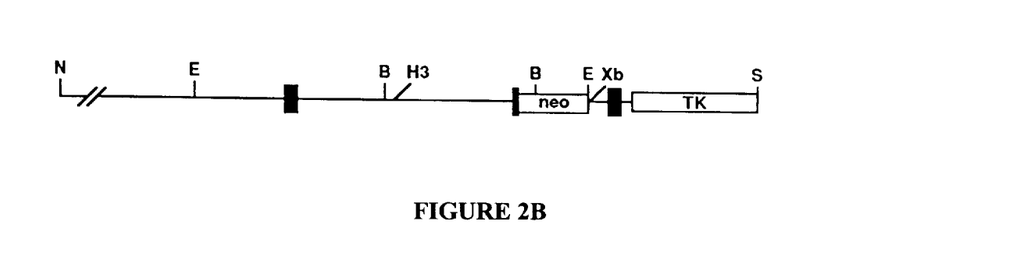
FIG. 2B illustrates the targeting construct employed in the preparation of disrupted RXRα constructs. Part of the B/Cl exon and adjacent intron are deleted by substitution of a PGK-neo cassette.
Figure 2C:
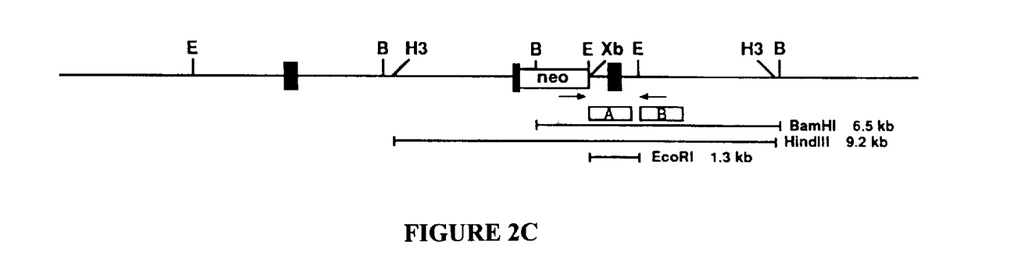

The organization of the 5' end of the RXRα gene is shown in FIG. 2A. The third exon (B/C1 exon) of the gene encodes the first part of the DNA binding domain, a domain which is required for receptor function. A targeting construct was prepared in which a PGK-neo cassette was introduced in an antisense orientation between an EcoRV site in the third exon and an XbaI site in the intron immediately downstream, so that part of the coding sequence, the splice donor, and the 5' part of the third intron are deleted. 15 kb of homologous sequence at the 5' side and 1 kb 3' drive homologous recombination of the targeting construct; a HSV-TK cassette was included to allow for negative selection against random integration events.

The targeting construct was introduced by electroporation into the J1 line of embryonic stem (ES) cells, and colonies isolated after selection in G418 and FIAU. Three colonies of a total of 77 screened were identified as homologous recombinants, and one of these colonized the germline when introduced into chimeric animals. Cell lines and animals were genotyped with two different probes on Southern blots, and by PCR analysis (see FIG. 2A). Probe A lies inside the targeting construct, whereas probe B lies approximately 0.5 kb outside; both probes gave identical patterns on blots with BamHI or HindIII digests of genomic DNA. This indicates correct single copy integration of the targeting construct by homologous recombination into the RXRα locus. PCR amplification using a neo-specific primer and a primer outside of the targeting construct confirmed this result.

Heterozygous offspring derived from germline transmission of the targeted allele were normal in all regards, and were crossed. From 18 litters, 83 pups were born, none of which were homozygous for the mutated allele, predicting an embryonic lethal phenotype (Table 1).

TABLE 1

Offspring of RXRα heterozygous crosses

|  | litters | Genotype* | | |
|---|---|---|---|---|
|  |  | +/+ | −/+ | −/− |
| E9.5 | 1 | 3 | 2 | 3 |
| E10.5 | 6 | 12 | 20 | 13 |
| E11.5 | 4 | 7 | 14 | 7 |
| E12.5 | 9 | 18 | 38 | 9 |
| E13.5. | 9 | 9 (1) | 33 | 10 (3) |
| E14.5 | 16 | 25 | 38 | 20 (1) |
| E15.5 | 5 | 10 | 18 | 7 (5) |
| E16.5 | 4. | 5 (1) | 14 | 4 (3) |
| E17.5 | 4 | 5 | 10 | 1 (1) |
| P > 1 | 18 | 20 | 63 | 0 |

*Offspring were taken midgestation at embryonic day E9.5–E17.5, or post-parturition (P > 1). Numbers in parentheses indicate embryos of the given genotypes which were found dead upon isolation, determined either by gross observation or by absence of blood flow when the umbilical cord was cut.

isolation of embryos in utero revealed a Mendelian frequency of live homozygotes through embryonic day 14.5 (E14.5), but a decreasing recovery at stages beyond (Table 1). Concurrently, an increasing number of dead embryos were seen at these later stages, and where tissue could be recovered for genotyping, often proved to be homozygotes, although a small number of nonhomozygous embryos were also seen which died in utero. The RXRα mutation therefore results in a period of embryonic lethality between E13.5 and E16.5, with most embryos viable at E14.5 and not by E15.5. It should be noted that these animals and embryos are not on a uniform genetic background, which may account for part of the observed variability.

RNA was isolated from embryos of normal appearance at E13.5, and analyzed for expression of the RXRα gene. Using a full length RXRα cDNA probe on Northern blots, a readily detectable transcript was surprisingly found, even in RXRα homozygous knockout embryos. Analysis by RT-PCR indicated that while no bona fide RXRα transcript is made in homozygous embryos, an aberrant transcript was produced which originates from within the neo gene cassette and which reads on the antisense strand of the neo coding sequence and the PGK promoter, through the third intron and into the fourth exon (C2) and beyond. Three novel bands are seen in homozygotes (and heterozygotes), but not in wildtype embryos, upon amplification with a neo-specific primer and a primer derived from the E domain of the RXRα gene. As established by cloning and sequencing, the upper band represents complete read-through of the third intron, the lower two represent cryptic splice donor sites in the third intron which are spliced to the fourth exon. In no case could an open reading frame be established contiguous with the RXRα coding sequence.

This analysis also detects a very low level of products of varying sizes in homozygotes when a primer from the second (A2) exon is used. The origin of these rare transcripts is not clear, but note that the second and fourth exons of the RXRα gene are out of frame with respect to each other, suggesting that even if a splice variant transcript was produced by skipping over the mutated third exon, the resultant transcript would also not encode a functional protein.

EXAMPLE 7

Analysis of RXRα Homozygous Embryos

Homozygous embryos recovered at various stages of embryonic development were analyzed microscopically and histologically. Homozygous embryos from E9.5 and E11.5 were normal and identical to wildtype and heterozygous littermates in size and appearance and in histological sections. The first manifestation of the RXRα mutation is evident at E12.5 in the embryonic liver and heart. The liver originates from the cardiac-hepatic eminence as an endodermal condensation below the emerging heart tube at E9.5, and is one of the first endodermal tissues to become morphologically recognizable. The liver increases in volume through midgestation, and by E12.5 is sufficiently developed in wildtype embryos to allow visualization through the skin by surface examination. In contrast, homozygous RXRα embryos are greatly deficient in the amount of liver present; this is seen in every embryo examined and is not a consequence of the amount of vascularization or blood flow present. By visual inspection, reconstruction of liver volume from serial sections, and by dissection and dry weight, it is estimated that E12.5 homozygous embryos have a liver mass of approximately 30% of wildtype littermates. As revealed by histological analysis, the hepatic tissue of RXRα homozygotes is of normal morphology. Despite the dramatic suppression of hepatic proliferation at E12.5, there is a substantial recovery, to approximately 60% of wildtype, by E14.5. This suggests that midgestation failure of liver proliferation is not likely to be a major contributor to the lethality seen in homozygous embryos. There was no indication that hematopoiesis, which occurs in the liver in early to midgestation embryos, was compromised in homozygotes.

Embryos at E14.5 appeared near normal in terms of size, shape, and overall developmental progress. Histological sections through homozygous and wildtype littermates indicated that most major organ systems were present and of normal appearance in homozygotes, including tissues in which RXRα is abundantly expressed, such as, for example, intestine, skin, and kidney. However, these embryos showed a swelling of the skin, sometimes quite dramatic, which upon histological analysis proved to be an edematous accumulation of fluid under the dermal layer of the skin. This edema was usually substantially pronounced in the folds of skin around the eye, causing a translucent appearance; the eye tissue itself was normal in these embryos.

EXAMPLE 8

Cardiac Defects in RXRα Homozygous Embryos

Generalized edema is often associated with defects in cardiac structure or function, and suggested the possibility of heart failure in RXRα homozygous embryos leading to accumulation of interstitial fluid. Normal heart development (reviewed by Litvin et al. in *Trends Cardiovasc Med.* 2:27–32 (1992)) involves the concerted differentiation of cardiogenic mesoderm, which gives rise to the myocardium and the endocardium, and the cardiac neural crest, from which migratory progeny populate the aorta, pulmonary artery, and associated structures. The myocardial component is comprised of ventricular trabeculae, which form a contractile lattice inside the ventricular chambers, and of the atrial and ventricular cardiac walls. The four chambers of the heart become distinct during midgestation by the formation of the atrioventricular valves and the interatrial and interventricular septa. Proliferation of myocytes at the ventricular epicardial surface (known as the compact zone) from E12.5 onward generates the thickened outer wall and contributes to the muscular interventricular septum which separates these two chambers.

As revealed by inspection of transverse sections at the level of ventricle inflow valves, the major defect in RXRα homozygous embryos was in the heart. Homozygous embryos at E12.5 appear comparable to wildtype littermates in the extent of ventricular wall thickness and total ventricular mass, but display other abnormalities. The contour of the ventricular surface is uneven, as is also manifest later. The visceral pericardial lining appears irregular, rather than tightly apposed to the ventricular wall, although later at E14.5 the pericardium appears relatively normal. Pericardial space was also very prominent in most embryos at this stage. An uneven ventricular surface and loosely apposed pericardium are features typical of E11.5 embryos. Homozygous embryos examined at E11.5 and earlier were identical to wildtype littermates, suggesting that the onset of developmental defects may occur around this time.

By E14.5, cardiac development in wildtype mouse embryos has proceeded to near maturity, in that all four chambers are present and separate, mitral and tricuspid valves are fully developed, and the aortic and pulmonary outflow tracts are separated and originate from opposite ventricles. The ventricles at this point are dense and muscular, both in terms of the thickness of the outer ventricular wall and in the extensive and well-organized trabeculation inside the ventricular chambers. In contrast, homozygous RXRα embryos display ventricular chamber hypoplasia, in which there is absence of proliferation of the compact muscular layer of the ventricular wall. Trabeculation inside the ventricle chamber is present but diminished, and frequently displayed disorganization at the muscular septum. This results in a ventricular septal defect in which a passage between ventricles could be observed, both between the ventricular septum and the endocardial cushion and through fenestrations in the septal tissue itself. All homozygous RXRα embryos displayed hypoplasia of the ventricular wall and (with one exception) obvious ventricular septal defects (Table 2).

TABLE 2

Cardiac abnormalities in RXRα embryos E14.5

| | RXRα Genotype* | | |
|---|---|---|---|
| | +/+ 6 embryos | −/+ 5 embryos | −/− 10 embryos |
| Ventricular chambers | | | |
| Wall mass decreased | 0/6 | 0/5 | 10/10 |
| Two chambers | 6/6 | 5/5 | 10/10 |
| Disorganized trabeculi | 0/6 | 0/5 | 10/10 |
| Ventricular septal defects | 0/6 | 0/5 | 9/10 |

TABLE 2-continued

Cardiac abnormalities in RXRα embryos E14.5

| | RXRα Genotype* | | |
|---|---|---|---|
| | +/+ 6 embryos | −/+ 5 embryos | −/− 10 embryos |
| Atrial chambers enlarged | | | |
| Left | 0/6 | 0/5 | 0/10 |
| Right | 0/6 | 1/5 | 5/10 |
| Atrial and Ventricular Valves | | | |
| Mitral atresia | 0/6 | 0/5 | 1/10 |
| Tricuspid atresia | 0/6 | 0/5 | 0/10 |
| Outflow tract abnormalities | | | |
| Aortic valve abnormal | 0/6 | 0/5 | 0/10 |
| Pulmonary valve abnormal | 0/6 | 0/5 | 0/10 |
| Aortic pulmonary septum abnormal | 0/6 | 0/5 | 1/9 |

*Serial 10 μ tissue sections were taken through the heart, stained with hematoxylin and eosin and photographed. Photos were scored independently three or four times for each of the listed features. In cases where the denominator does not equal the total number of fetuses examined, the sections were damaged such that an accurate assessment could not be made.

The aorta and pulmonary artery outflow tracts and valves, which depend on the influence of cardiac neural crest progeny for proper differentiation, appeared normal and were properly septated in all but one embryo. In some cases the right ventricle appeared dilated, and enlarged right atria were frequently seen, while mitral atresia was seen in one embryo. It is likely that the primary defect in RXRα mutant embryos is in the differentiation or maturation of the ventricular cardiac myocytes, which is compromised in all homozygous embryos. Defects seen only sporadically are presumably secondary to hemodynamic disturbances caused by decreased cardiac performance.

The cardiac dysmorphogenesis of homozygous embryos did not completely abolish all organized cardiac contractions, as the ventricular chambers could be observed to pump and blood flowed from the umbilical cord when it was severed. However, cardiac function in the affected embryos is likely to be severely compromised by the hypoplasia of the ventricular chamber wall, which is responsible for generating the systolic force of embryonic blood flow. At E14.5, the embryo is beginning a phase of exponential growth, increasing in weight over 50% per day (see Kaufman in *The Atlas of Mouse Development,* Harcourt Brace Jovanovich: San Diego (1992)). It is almost certain that homozygous embryos die in utero from an inability of the defective hearts to provide a sufficient flow of blood to sustain this rapid growth, resulting in a form of embryonic congestive heart failure.

While the invention has been described in detail with reference to certain preferred embodiments thereof, it will be understood that modifications and variations are within the spirit and scope of that which is described and claimed.

What is claimed is:

1. A transgenic mouse embryo whose genome comprises a homozygous disruption of the endogenous RXRα gene, wherein said disruption comprises the insertion of a targeting construct, and wherein said disruption results in hypoplastic development of the heart in said mouse embryo.

2. A cell line isolated from the transgenic mouse embryo of claim 1, wherein said cell line comprises said disruption of the endogenous RXRα gene.

3. A method to determine the selectivity of a ligand for RXRα, said method comprising:

treating the transgenic mouse embryo of claim 1 with a ligand, wherein said ligand produces an RXRα-mediated response in a wild-type mouse, and wherein an absence of the RXRα-mediated response in the transgenic mouse embryo identifies the ligand as having selectivity for RXRα.

4. A transgenic mouse whose genome comprises a heterozygous disruption of the endogenous RXRα gene, wherein said disruption comprises the insertion of a targeting construct, and wherein said disruption results in hypoplastic development of the heart in a transgenic mouse embryo whose genome is homozygous for said disruption.

* * * * *